United States Patent
Irion

(10) Patent No.: US 6,863,650 B1
(45) Date of Patent: Mar. 8, 2005

(54) ENDOSCOPIC INSTRUMENT FOR PERFORMING ENDOSCOPIC PROCEDURES OR EXAMINATIONS

(75) Inventor: Klaus M. Irion, Liptingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/488,500

(22) Filed: Jan. 20, 2000

Related U.S. Application Data

(63) Continuation of application No. PCT/EP98/04575, filed on Jul. 21, 1998.

(30) Foreign Application Priority Data

Jul. 24, 1997 (DE) .......................................... 197 31 894

(51) Int. Cl.⁷ ............................... A61B 1/00; A61B 1/04
(52) U.S. Cl. ........................................ 600/104; 600/117
(58) Field of Search ................................. 600/101, 104, 600/117, 139; 606/205–209

(56) References Cited

U.S. PATENT DOCUMENTS

| 4,541,438 A | * | 9/1985 | Parker et al. .............. 424/9.61 |
| 4,918,000 A | * | 4/1990 | Schubert ......................... 435/7 |
| 6,258,576 B1 | * | 7/2001 | Richards-Kortum et al. ..... 435/172 |
| 6,294,331 B1 | * | 9/2001 | Ried et al. ..................... 435/6 |

* cited by examiner

*Primary Examiner*—Justine R. Yu
*Assistant Examiner*—Fenn C. Mathew
(74) *Attorney, Agent, or Firm*—St. Onge Steward Johnston & Reens LLC

(57) ABSTRACT

An endoscopic instrument, comprises a shaft, a handle arranged at a proximal end of said shaft, at least one working part arranged at a distal end of said shaft, and at least one marking having a fluorescing substance that can be excited to fluoresce by a light source, said marking is provided at a distal end section of said instrument. Said fluorescing substance is selected in such a way that its exciting range lies in an excitation range of a tumor-specific photosensitizer or in an excitation range of a tissue autofluorescence.

44 Claims, 2 Drawing Sheets

ENDOSCOPIC INSTRUMENT FOR PERFORMING ENDOSCOPIC PROCEDURES OR EXAMINATIONS

CROSSREFERENCE OF PENDING APPLICATION

This application is a continuation of pending international application PCT/EP 98/04575 filed on Jul. 21, 1998.

BACKGROUND OF THE INVENTION

The present invention relates to an endoscopic instrument for performing endoscopic procedures or examinations, having a shaft, a handle arranged at the proximal end of the shaft, and at least one working element arranged at the distal end of the shaft, in particular mouth parts.

The invention further relates to an endoscopic instrument suite that contains such an endoscopic instrument and also a light-supplying apparatus and an endoscopic observation instrument, in particular an endoscope, that is connected to a light source.

Endoscopic instruments and endoscopic instrument suites of this kind are commonly known, and are used in the increasingly widespread practice of minimally invasive surgery.

The methods of photodynamic diagnosis (PDD) and photodynamic therapy (PDT) are increasingly being used in endoscopy to detect and treat tissue changes. The offprint from Endo World, URO No. 17/1-D, 1997, "Photodynamic diagnosis (PDD) for early detection of bladder carcinoma" [Photodynamische Diagnose (PDD) zur Früherkennung des Harnblasenkarzinoms] of Karl Storz GmbH & Co., Tuttlingen, Germany, discloses a system used, in conjunction with a photosensitizer that accumulates in tumor-specific fashion and exhibits fluorescence under specific excitation light, to detect tumors or malignant tissue changes. Aminolevulinic acid (ALA), for example, is used successfully as a precursor of a photosensitizer of this kind.

It is known from U.S. Pat. No. 5,408,996 to detect malignant tissue endoscopically by causing fluorescence of a marking substance conveyed to the tissue.

Tissue changes can also be detected on the basis of "autofluorescence" triggered by natural fluorescent substances occurring superficially in external tissue layers.

In all these methods, light (called "excitation light") in a specific wavelength range is coupled into the tissue region containing the fluorescent substance, and that fluorescent substance is thereby excited to fluoresce. The fluorescence wavelength range is always of longer wavelength than the excitation range. When ALA is used as the precursor for the tumor-specific photosensitizer photoporphyrin, excitation is performed in the blue (380 to 340 nm), and fluorescence occurs in the red (635 nm). The manner in which fluorescent excitation, as opposed to normal or so-called "white" light, can make a tumor visible in clearly defined fashion is strikingly evident from page 5 of the aforementioned "Endo World" brochure. Even tiny satellite tumors of a fluorescing papillary tumor can be detected in a manner clearly differentiated from the principal tumor, and can be appropriately treated or removed in a surgical endoscopic procedure.

In autofluorescence examinations, the excitation can also occur in the blue and the fluorescence appears principally in the green and red spectral region. Excitation can also be performed in the UV range.

Since the fluorescence intensity is much lower than the excitation intensity, the spectral region of the excitation light is almost completely blocked out in the receiving observing system by filters, to allow detection of the fluorescent emission. Only the fluorescing areas are clearly visible.

This has the disadvantageous consequence that when instruments are introduced into the region illuminated and imaged by the endoscope, these instruments are difficult or in fact impossible to detect when the illumination system is operating in fluorescence mode. In other words, a surgeon watching the surgical procedure via an endoscope, cannot see the instrument in the fluorescence illumination mode. It has therefore hitherto been necessary to switch over continually from fluorescence mode to white-light mode, and vice versa, in order to bring an instrument accurately to the tissue area that is to be examined or treated. This is cumbersome, extremely laborious and irritating to the surgeon, and most of all hazardous or critical in terms of the procedure.

These instruments can be of many different kinds. They can be instruments used in examinations (diagnosis) or also in surgical procedures (therapy).

It is fundamentally known from DE 39 33 199 C2 to equip the distal end piece of a flexible endoscope with a marking which makes it possible to view the end piece in the context of X-ray examinations.

It is the object of the present invention to create an endoscopic instrument that is clearly detectable even in fluorescence mode, and to create an endoscopic instrument with which endoscopic surgical procedures or examinations can be performed under fluorescence conditions.

SUMMARY OF THE INVENTION

According to the present invention, the endoscopic instrument is provided with at least one marking having a fluorescing substance that can be excited to fluoresce by a light source, said marking is provided in the distal end section at the instrument.

In one embodiment, the fluorescing substance is selected in such a way that its excitation range lies in the excitation range of a tissue autofluorescence.

It is preferred in this context if the fluorescing substance can be excited in a range from 400 nm to 500 nm.

The considerable advantage of this feature is that because, as mentioned earlier, tissue autofluorescence is extremely weak, the excitation frequency used is not a different one that interferes with that autofluorescence but instead precisely the same excitation range, so that then the corresponding fluorescence is obtained in the same way as the autofluorescence.

In another embodiment, the fluorescing substance is selected so that its excitation range lies in the excitation range of a tumor-specific photosensitizer.

In the context of this embodiment, it is particularly preferred to perform excitation in an excitation range from 370 nm to 440 nm.

This feature has the general advantage that excitation is performed only with a very specific excitation range, and fluorescence is produced both in the tumor and also on the marked instrument. Mutual interfering influences upon excitation of the tumor-specific photosensitizer on the one hand and of the fluorescing substance of the marking on the other hand are then no longer possible, and are thus inherently ruled out by the system. The aforementioned wavelength range in the range from 370 nm to 440 nm is an excitation range for exciting the photosensitizer induced by ALA that is usable for marking tumors.

A "light source" for the purposes of the present invention is understood to be a radiation source that radiates light in the UV, visible, and/or IR range. Unlike X-ray light, light in this wavelength range does not adversely affect or even damage the tissue of the body being examined or treated, or the observer, so that even extended operations, or numerous surgical procedures performed by the surgeon in fluorescence mode, can be carried out without radiation damage.

Because of the fluorescent marking, it is now possible to clearly recognize an instrument in fluorescence mode and moreover to determine unequivocally its position relative to the tissue that is to be examined or removed. As a result it is easily possible, under fluorescent diagnostic light conditions, to bring, for example, a biopsy forceps or another instrument, for example a laser fiber, to the fluorescing tumor area under endoscopic observation and, for example, to take a tissue sample, with no need to switch over to standard endoscopic white-light illumination. It is thus possible to work continuously during the procedure in fluorescence mode, in which both the tumor to be treated and the instrument used for the purpose, or its working elements, are clearly and unequivocally recognizable. This thus creates the possibility of performing both photodynamic diagnosis (PDD) and photodynamic therapy (PDT) under consistent light conditions for the surgeon, i.e. with no switching between white light and fluorescence mode.

In the case of the endoscopic instrument suite, the light source is selected in such a way that the fluorescing substance on the endoscopic instrument can be excited thereby.

Provision can be made for both the fluorescing substance on the endoscopic instrument and the fluorescing substance in the tissue to be excitable by one and the same light source and for each to exhibit fluorescence of the same color; provision can also be made for operating it with different wavelengths, and accordingly achieving different fluorescence phenomena. The fluorescing substance can be applied directly onto the instrument or can be incorporated into it. It is, of course, always applied at a point that is located in the observation region of an endoscope.

In a further embodiment of the invention, the marking is configured as a marking element applied on the instrument.

The advantage of this feature is that the endoscopic instrument is manufactured in the usual manner and then, if that instrument is intended for fluorescence mode, the marking element with the desired fluorescing substance can be applied.

In a further embodiment of the invention, the marking element is applied removably.

The advantage of this feature is that the marking element can be removed, for example for cleaning purposes or if the endoscopic instrument is also to be used in nonfluorescing mode. This also creates the possibility of applying correspondingly selected or suitable marking elements to the endoscopic instrument for different kinds of operations, or if different tissues are to have different photosensitizers added to them.

In a further embodiment of the invention, the at least one distal working element is equipped with a marking.

The considerable advantage of this feature is that by providing the marking on the working element, the surgeon can detect with particular precision the point at which the working element is currently located, for example in order to begin and perform a surgical procedure precisely.

In a further embodiment in which the working elements are configured as two mouth parts, provision is made for them each to be equipped with a marking.

The considerable advantage of this feature for the surgeon is that he or she can bring, for example, the piece of tissue that is to be detached precisely between the two spread mouth parts, i.e. can accurately establish the position of the spread mouth parts relative to the piece of tissue (also marked) that is to be detached, and can then detach the tissue at a precisely determined and appropriate point.

In a further embodiment of the invention, both the working element and the proximal end section of the shaft are each equipped with a marking.

This feature offers the advantage for the surgeon not only that he or she can determine the position of the shaft relative to the working elements, e.g. mouth parts, but also that this embodiment can be utilized in particularly favorable fashion for "instrument tracking." In instrument tracking, the endoscopic imaging system (endoscope, camera) or the endoscopic image always tracks the manipulating instrument. It is known from DE 195 29 950 C1 to perform instrument tracking on the basis of large-area color markings on instruments. In the body itself, however, all possible colors of the visible region can occur, and it is therefore impossible for a color datum acquired by the endoscope to be assigned unequivocally to the instrument.

At present, an assisting surgeon guides the camera with the proximally-mounted camera. The disadvantage associated with this is that in long operations, manual tracking of the endoscope is no longer performed with the necessary accuracy because the assistant exhibits symptoms of fatigue, so that for brief periods the surgeon is temporarily unable to see the surgical field. The endoscope may move back and forth due to fatigue symptoms, so that image quality is decreased by blurring. In this configuration, "solo surgery" cannot be performed with the instrument suite. The provision of multiple markings, or of markings that extend over a larger surface region, now creates the possibility of accomplishing automatic tracking by way of the fluorescent markings, since the particular three-dimensional position can be exactly determined by the equipment. If the position of the instrument having the markings is then changed by the surgeon, the image sensing system can detect this change in position and the observation system, for example the endoscope, can be correspondingly shifted, i.e. "tracking" can be performed. For example, external 3-D sensors which continuously sense the position of the instrument can be employed so that via an endoscope control device, the working area of the instrument is always automatically made to coincide with the endoscope image.

In a further embodiment of the invention, the marking element is configured as a tubular bushing that can be slid onto a tubular shaft.

The advantage of this feature is that the marking element can easily be slid onto the shaft. If this tubular bushing already has a specific geometric extent, multiple definition points (for example its beginning and its end) can already be utilized for spatial positioning with respect to a fixed reference point.

In a further embodiment of the invention, the marking element has a coating made of transparent glass, or a transparent plastic coating, that covers the fluorescing substance.

The advantage of this feature is that the actual fluorescing substance is hermetically isolated from the surgical field, but nevertheless can be excited to fluoresce through the transparent coating. As a result, it is then also possible to use fluorescing substances that are not intended to come into contact with bodily fluids, either because their fluorescence properties are thereby changed or because those substances can be damaging to the tissue. The selection of fluorescing substances usable in the medical field is also substantially broadened thereby.

In a further embodiment of the invention, the marking element is configured such that it can be inserted into the body on which the endoscopic procedure is being performed, and can be anchored there.

The advantage of this feature is that, for example in an initial diagnostic step, a marking can be left behind or anchored so that the location can be immediately recognized again in a subsequent surgical procedure. In a surgical procedure that is possibly performed by a surgical team other than the one performing the diagnostic step, fluorescent excitation can be used for immediate detection of the specially shaped marking and consequently also of the tissue, marked with that marking, that is to be treated.

In a further embodiment of the invention, the fluorescing substance is selected from the group comprising fluorescein, Acridine Orange, the tetracyclines, eosin, cadmium sulfide, aminolevulinic acid, aminolevulinic acid hydrochlorides, porphyrins, rhodamine B, rhodamine G, auramine, auramine Carbol Fuchsin, and Nile Blue sulfate.

These are common fluorescing substances or "fluorochromes."

In a further embodiment of the invention, the fluorescing substance is selected so that it can be excited to fluoresce in the wavelength range from 200 to 900 nm.

This wavelength range, which extends on either side beyond the visible light wavelength range from 400 nm to 750 nm, offers a wide range of applications. For example, excitation can occur in the invisible UV range, thus achieving fluorescence in the visible range. This feature has the advantage, for example, that the excitation light is not perceptible and not disturbing to the surgeon, who perceives only the fluorescence in the visible range.

This also creates the further possibility of performing excitation, for example, in the invisible UV range and achieving fluorescence in the (also invisible) infrared range. This will be advantageous if, for example, automatically monitored actions are taking place, for example instrument tracking, which can take place without influencing the surgeon's eye.

In this kind of embodiment of the invention the fluorescing substance is selected, for example, so that it can be excited to fluoresce in the wavelength range from 320 to 380 nm, i.e. by invisible UV light, and fluorescence can then occur in the visible range.

In a further embodiment of the invention, multiple markings with differently excitable fluorescing substances are provided.

The considerable advantage of this feature is that an instrument of this kind can be used flexibly for different diagnostic or surgical procedures or in conjunction with different tumor-specific photosensitizers, since because of the presence of the differently excitable fluorescing substances, at least one substance that is excitable for the specific purpose is then always present.

This capability can also advantageously be used in "instrument tracking". For example, one or more markings that can be excited outside the visible range and that optionally fluoresce outside the visible range can be utilized for tracking, and a further marking can be used as a marking visible to the surgeon.

In a further embodiment of the invention, multiple markings, which contain different concentrations of fluorescing substances, are present.

The advantage of this feature is that depending on local conditions and the fluorescence intensity of the tumor, it is possible to work in correspondingly compensated fashion, i.e. at high or low intensity.

Marking in this fashion with differently excitable fluorescing substances also makes it possible, when setting up an endoscopic instrument suite with, for example, an endoscope and a video camera, to establish an optimum irradiation intensity by way of the excitation light source at the beginning of the operation.

In a further embodiment of the invention, the marking has a fluorescing substance corresponding to that of a marking element inserted into the body.

This feature, in combination with the previously mentioned feature of the marking element inserted into the body, has the advantage that it is possible to work with one and the same excitation system, so that both marking elements already inserted into the body, and the endoscopic instrument equipped with the corresponding marking, are clearly recognizable by the surgeon and, for example, the inserted element can also easily be grasped and removed again with the medical instrument.

In the case of the endoscopic instrument suite, which has in addition to the endoscopic instrument a light-supplying apparatus and an endoscopic observation instrument, in particular an endoscope, that is connected to an light source, it is furthermore advantageous that at least one endoscopic manipulation instrument, in particular a trocar, is provided, through which the observation instrument can be introduced into the body, at least one marking with a fluorescing substance corresponding to the endoscopic instrument being provided on the inner side of the manipulation instrument.

The considerable advantage of this feature is that the functionality of a PDD or PDT system can be tested in vivo using an intracorporeal reference. When the instrument, coated with the fluorescing substance, is slid into the trocar, the functionality of the system can be checked by way of the fluorescing substance distributed over the inner side surface. It is in fact additionally possible to adjust various parameters—for example sufficient power density of the excitation light or the spectral composition of the excitation light—optimally for the particular application. In addition, an optimum color adjustment for a camera sensing the endoscopic image can be performed.

In the case of an endoscopic instrument suite of this kind, it is further advantageous that the observation instrument is an endoscope that is equipped with an endoscopic camera.

The advantage of this feature is that the surgeon need not work directly at the endoscope, but that instead the image is acquired via an endoscopic camera, so that is it thus possible to store that image information, for example in order to identify changes upon subsequent examinations or to convey the image information to an image processing system for better processing. For example, information that was obtained in a diagnostic procedure can be compared, at the beginning of an operation, to the data acquired at that time and, for example, progression of the tumor or perhaps even shrinkage as a result of other chemical treatments can be detected. This also makes it possible to sense the decrease in fluorescence during a PDT treatment (PDT dosimetry), for example by way of marked elements left in the body.

In a further embodiment of the invention, there is provided downstream from the endoscopic camera an image processing system that continuously detects the fluorescing markings in the endoscopic image.

The advantage of this feature is that because of the image processing system, it is possible by way of suitable filters to suppress interfering or undesired fluorescence phenomena or to amplify weak signals. so that the surgeon is provided with an optimal image of both the tissue and the marked instrument.

In a further embodiment of the invention, the light source emits pulsed light at least in the spectral excitation range of the fluorescing substance, the pulse frequency corresponding to the video image frequency or video frame frequency of the endoscopic camera.

The advantage of this feature is that precise instrument tracking can be performed with this pulsed technique and that even very small changes in position, which cannot be perceived by the human eye, can be sensed. The PAL standard is 25 and 50 Hz, and the NTSE standard 30 and 60 Hz. The pulsed technique allows instrument tracking without thereby influencing or disturbing the human eye, since at the image frequencies usual in video technology, the human eye is too slow-reacting to perceive differences.

In a further embodiment of the instrument suite, provision is made for the observation instrument to have, at the distal end, a transparent element having a fluorescing substance.

The considerable advantage of this embodiment is that reflected light received by the observation instrument, which lies in the nonvisible region, can be converted into a visible fluorescence phenomenon by the fluorescing substance that is excited in that region.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be explained and described in more detail below with reference to a selected exemplary embodiment.

In the drawings.

DETAILED DESCRIPTION OF PREFERRED EMBODIMENTS

Figure 1:
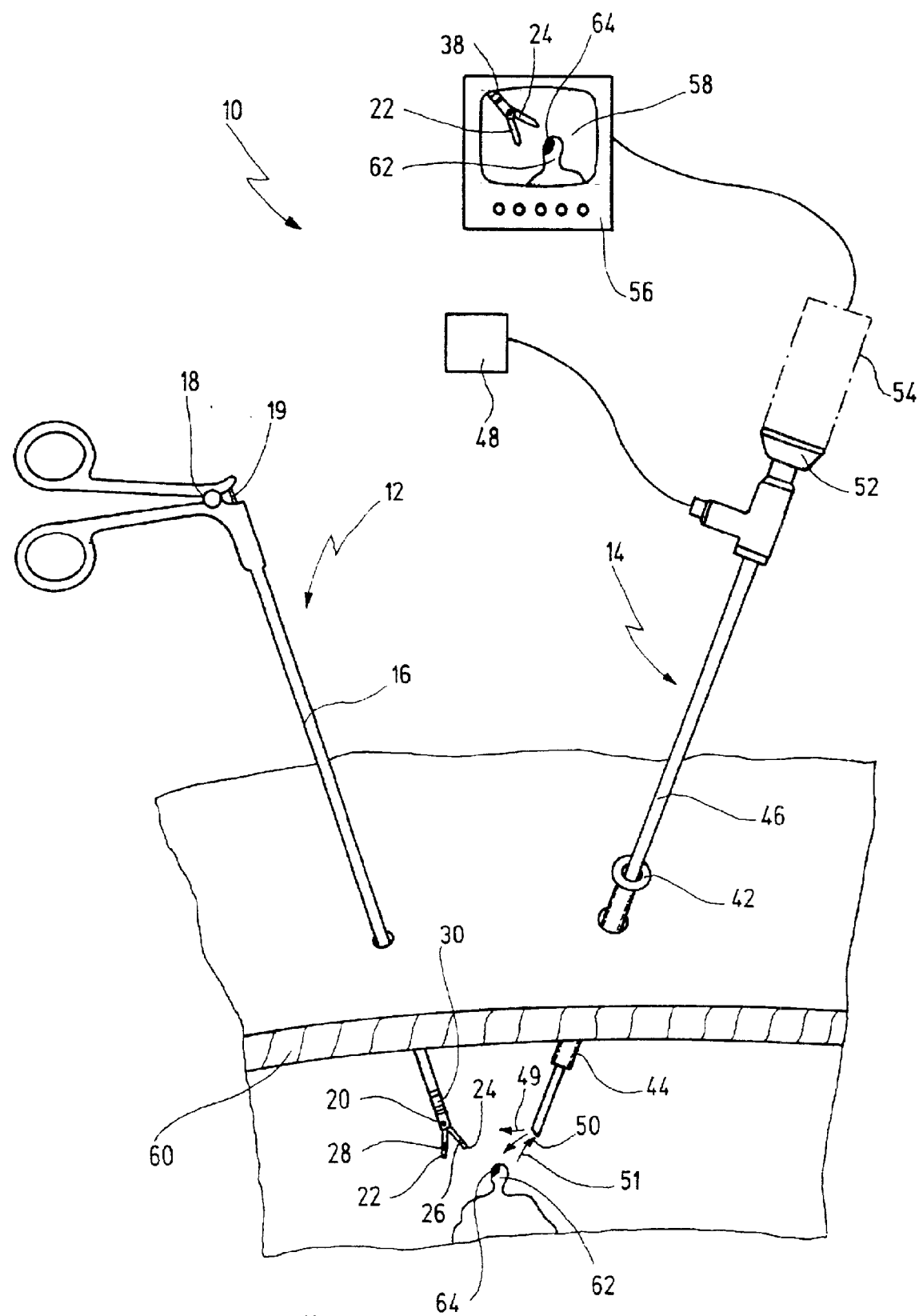
FIG. 1 shows a highly schematized view of an endoscopic instrument suite during an endoscopic procedure.

In FIG. 1, an endoscopic instrument suite is labeled in its entirety with the reference number 10.

Endoscopic instrument suite 10 has an endoscopic instrument 12 and an endoscope 14.

Endoscopic instrument 12 is a grasping forceps that has an elongated tubular shaft 16. At the proximal end, shaft 16 is equipped with a handle that comprises two scissor-like handle elements interconnected via a hinge. A working element 20, in the form of two mouth parts 22 and 24, is arranged at the distal end.

Mouth parts 22 and 24 are connected to the handle via an actuating element 19, so that pivoting of the movable handle element causes a linear movement of actuating element 19 along shaft 16, and mouth parts 22 and 24 are spread or closed depending on the direction of movement.

Figure 2:
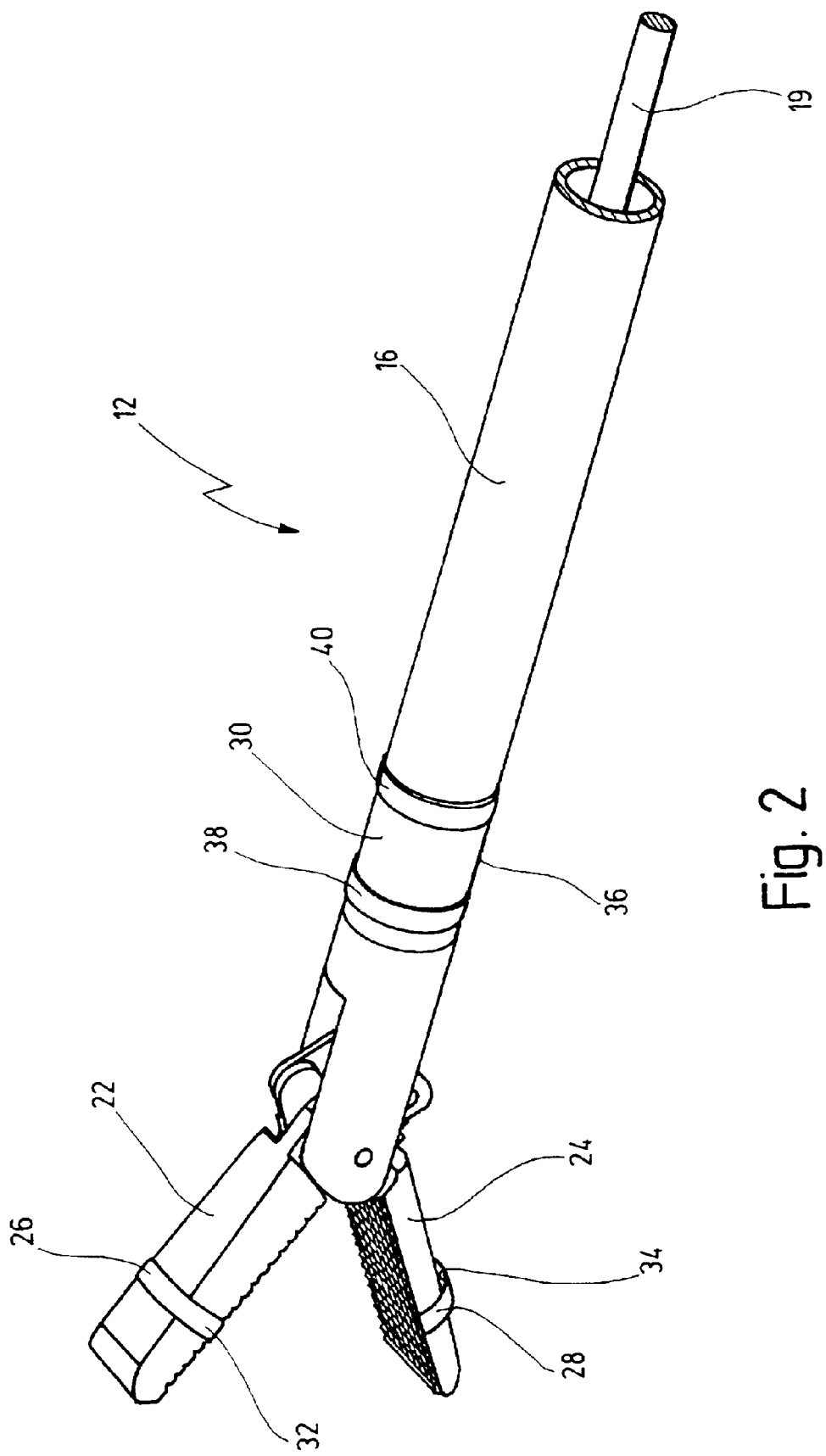
FIG. 2 shows a greatly enlarged partial perspective view of the distal end section of the endoscopic instrument that is used in this operation.

As is evident from the enlarged partial presentation of FIG. 2, each mouth part 22 and 24 is equipped with a marking 26 and 28. In addition, a further marking 30 is provided in the region of the distal end of shaft 16.

Markings 26 and 28 of mouth parts 22 and 24 comprise separately attachable marking elements 32 and 34.

Marking elements 32 and 34 are of semicircular configuration, and can be clipped in immovably adhering fashion from the outside onto mouth parts 22 and 24.

Each marking element 32 and 34 comprises a transparent plastic double film between which a fluorescing substance is embedded. A "fluorescing substance" is understood to be a substance that exhibits fluorescence following excitation with light of a specific wavelength range. The wavelength range of the excitation light lies in the range from 200 nm to 900 nm, i.e. encompasses the range of visible light (approximately 400 nm to 750 nm) as well as the invisible UV and IR regions.

Marking 30 comprises a tubular bushing 36 that is slid onto the outer side of shaft 16 and has a respective marking ring 38 and 40 at its opposite ends.

Marking rings 38 and 40 also contain a fluorescing substance, which can be the same as the fluorescing substance of marking elements 32 and 34 or can also be a different fluorescing substance, for example a substance that can be excited in the UV range and exhibits fluorescence in the IR range.

Endoscope 14 has an endoscope shaft 46 that is introduced, through a manipulation instrument 42 in the form of a trocar 44, into a body cavity through an abdominal wall 60 of a human body.

Endoscope shaft 46 is joined proximally, via a lateral extension, to a light source 48. Light source 48 can radiate ultraviolet (UV), visible, and/or infrared (IR) light; very specific wavelength ranges, and multiple defined wavelength ranges, can also be radiated. Endoscope shaft 46 contains light guides in the form of a glass-fiber bundle which delivers at the distal end of endoscope shaft 46 the light proceeding from light source 48, as indicated by arrows 49.

Also received in endoscope 14 is an optical system 50 that comprises a rod lens system, arranged in endoscope shaft 46, which ends at the proximal end in an eyepiece equipped with an eyepiece cup 52. Fluorescent light incident at the distal end of endoscope shaft 46, as indicated by an arrow 51, can thus be guided through the optical system to the distal end of endoscope 14.

If, for example, a tissue sample is to be taken from a tissue 62 present in the body, both endoscopic instrument 12 and endoscope 14 are introduced, in a manner known in the minimally invasive surgical technique, through small body openings, e.g. through abdominal wall 16. These body openings are usually created by way of trocars or their trocar mandrels. Following insertion of both endoscopic instrument 12 and endoscope 14, the surgeon can place his or her eye against eyepiece shell 52 and observe the regions visible in the abdominal cavity beneath abdominal wall 16. In the above-described technique of photodynamic diagnosis (PDD), a precursor of a photosensitizer, e.g. aminolevulinic acid (ALA), has previously been administered to the patient. If a tumor 64 is present in the region of tissue 62 being examined, the ALA photosensitizer precursor accumulates in it, and the accumulated fluorescing substance can be excited by a corresponding excitation light, in this case in the blue (380 nm to 430 nm), to fluoresce via a specific conversion process, this fluorescence occurring in the red (635 nm). If the tissue 62 shows autofluorescence one can excite to autofluorescence in the respective excitation range of the tissue, for example in the range from 400 nm to 500 nm. As described earlier, light source 48 is configured such that it emits either white light or a special light in the ALA excitation range, i.e. blue light from 380 nm to 430 nm. If a medical instrument were made of medical steel, as is usual for endoscopic instruments 12 in the form of a grasping forceps for removing a tissue sample, this forceps would be very difficult to detect. Because endoscopic instrument 12 is now equipped with markings 26, 28, and 30, these markings are also excited to fluoresce. In the simplest case, the marking is selected so that it contains a fluorescing substance that can also be excited with blue light and exhibits fluorescent phenomena in red light. The surgeon can thus detect, via optical system 50 of endoscope 14, both fluorescing tissue 62 and also fluorescing markings 26, 28 and optionally also 30 of endoscopic instrument 12, and thus can remove the tissue sample precisely using endoscopic instrument 12. In the case of a surgical procedure, endoscopic instrument 12 can be configured as a cutting forceps that detaches, for example, a tissue area affected by a tumor 64.

In FIG. 1, the dot-dash line indicates an endoscopic camera 54 that is placed onto eyepiece shell 52 of endoscope 14. Endoscopic camera 54 is connected to an image processing system 56 that generates a video image 58 on a monitor.

In this instance the surgeon can observe the surgical region by way of the monitor. It is evident from video image 58 that at the aforementioned excitation frequency at which the precursor ALA exhibits fluorescence by conversion into photoporphyrin, this occurs to a greater extent in the region of a tumor 64 on tissue 62. Also visible on video image 58 is the distal end region of endoscopic instrument 12, or at least the markings of mouth parts 22 and 24. It is thus possible to remove in very specific fashion, for example, a tissue sample in the region of tumor 64.

The interposition of an image processing system 56 makes it possible to perform instrument tracking, i.e. endoscope 14 can be displaced via an actuating drive (not shown here in further detail). For this purpose, light source 48 radiates pulsing light that specifically excites marking 38, and also optionally markings 26 and 28 on mouth parts 22 and 24, to fluoresce. With these three location parameters, the three-dimensional position of endoscopic instrument 12 relative to endoscope 14 can be sensed via external 3-D sensors, and can be coupled to the actuating drive for the endoscope. If the position of endoscopic instrument 12 is then changed, this is sensed by image processing system 56 which sends a corresponding signal to the actuating drive, which then brings endoscope 14 into a position such its optical sensing region at the distal end once again senses the distal end of endoscopic instrument 12. Thus as the surgeon, for example, approaches tumor 64 of tissue 62 with endoscopic instrument 12, the control system is such that mouth parts 22 and 24, and marking 38 on the distal end section of shaft 38, are always within the optical field of view of optical system 50.

Present on the inner side of trocar sleeve 44 are markings with numerous fluorescing substances, for example including the fluorescing substances that are present on mouth parts 22 and 24 and on marking 38; ALA is optionally also present as a reference substance. When the distal end of endoscope shaft 46 is slid in through trocar 14, it is thereby possible to put light source 48 and image processing system 56 into service even before the distal end has penetrated into the body cavity, in order to ascertain whether the system is working; image compensation can also be performed at the same time. If the pulsing is performed, for example, at the video frequency of the camera system (50 Hz for PAL, 60 Hz for NTSC), the marked point can then be determined very easily by referencing the color values of successive frames. Because of the relatively high frequency, a human observer cannot resolve the color differences in time, and therefore does not perceive the disruptive difference. The same applies in the case of an excitation in the visible and a specific fluorescence in the IR region.

Using sensing by way of at least two spatially associated image sensors, instruments marked with fluorescent substances make possible position detection, i.e. localization of the spatial instrument coordinates or direction. Because these points are marked with fluorescing substances that radiate differently in terms of wavelength and/or are marked differently in terms of surface extent, no ambiguity in allocation occurs in the image sensing chips. This also creates the possibility for image processing system 56 to detect not only where endoscopic instrument 12 is located, but also whether the correct instrument is being used.

What is claimed is:

1. An endoscopic system comprising an endoscopic instrument and a light source, said endoscopic instrument comprising:

a shaft, a handle arranged at a proximal end of said shaft, at least one working part arranged at a distal end of said shaft, and at least one fluorescent marking, having a fluorescing substance that can be excited to fluoresce by a light source, said marking is provided at a distal end section of said endoscopic instrument, wherein said fluorescing substance is selected in such a way that its excitation range lies in an excitation range of a tumor-specific photosensitizer applied to tissue surrounding said endoscopic instrument, said light source is selected in a way that it only emits light of specific wavelength ranges matching excitation ranges of both said fluorescent marking of said instrument and the tissue surrounding said endoscopic instrument to which said tumor specific photosensitizer has been applied, therefore said same light source can excite both fluorescence phenomena.

2. The endoscopic system of claim 1, wherein said fluorescing substance is selected to be excited in a range from 370 nm to 440 nm.

3. The endoscopic system of claim 1, wherein said marking is configured as a marking element applied on said endoscopic instrument.

4. The endoscopic system of claim 3, wherein said marking element is applied removably.

5. The endoscopic system of claim 1, wherein said at least one distal working element is equipped with said marking.

6. The endoscopic system of claim 5, wherein two working elements are present and are configured as two mouth parts that are each equipped with a marking.

7. The endoscopic system of claim 1, wherein a marking is respectively provided both on said at least one working element and in a distal end section of said shaft.

8. The endoscopic system of claim 1, wherein said shaft is configured as a tubular shaft, and wherein said marking is configured as a tubular bushing that can be slid onto said tubular shaft.

9. The endoscopic system of claim 1, wherein said marking is provided with a coating, made of a transparent material, that covers said fluorescing substance.

10. The endoscopic system of claim 1, wherein said marking is configured as a marking element applied on said endoscopic instrument, said marking element can be inserted into a body on which an endoscopic procedure is being performed, and said marking element can be anchored there.

11. The endoscopic system of claim 1, wherein said fluorescing substance is selected from the group consisting of fluorescein, eosin, the porphyrins, cadmium sulfide, aminolevulinic acid, aminolevulinic acid hydrochloride, Acridine Orange, tetracyclines, auramine, rhodamine B, rhodamine G, auramine Carbol Fuchsin, and Nile Blue sulfate.

12. The endoscopic system of claim 1, wherein multiple markings with differently excitable fluorescing substances are provided.

13. The endoscopic system of claim 1, wherein multiple markings containing different concentrations of said fluorescing substance are present.

14. The endoscopic system of claim 1, wherein said marking is configured as a marking element that can be inserted into a body on which an endoscopic procedure is being performed, and can be anchored there, and wherein said marking element has a fluorescing substance corresponding to said of a further marking element inserted into said body.

15. The endoscopic system of claim 1, further containing a light-supplying apparatus and an endoscopic observation instrument that is connected to a light source, selected in such a way that said fluorescing substance can be excited to fluoresce by said light source.

16. The endoscopic system of claim 15, wherein said observation instrument is an endoscope.

17. The endoscopic system of claim 16, wherein said endoscope is equipped with an endoscopic camera.

18. The endoscopic system of claim 17, wherein there is provided downstream from said endoscopic camera an image processing system that continuously detects said fluorescing markings in an endoscopic image.

19. The endoscopic system of claim 1, wherein at least one endoscopic manipulation instrument is provided, through which an observation element can be introduced into a body, and at least one marking with a fluorescing substance corresponding to the marking of said endoscopic instrument is provided on an inner side of said manipulation instrument.

20. The endoscopic system of claim 19, wherein said manipulation instrument is a trokar and said observation element is an endoscope.

21. The endoscopic system of claim 18, wherein said light source emits pulsed light at least in a spectral excitation range of said fluorescing substance, and a pulse frequency corresponds to a video image frequency of said endoscopic camera.

22. The endoscopic system of claim 20, wherein said observation instrument has, at a distal end thereof, a transparent element having a fluorescing substance.

23. An endoscopic system comprising an endoscopic instrument and a light source, said endoscopic instrument comprising:
   a shaft,
   a handle arranged at a proximal end of said shaft,
   at least one working part arranged at a distal end of said shaft, and
   at least one fluorescent marking, having a fluorescing substance that can be excited to fluoresce by a light source, said marking is provided at a distal end section of said endoscopic instrument,
   wherein said fluorescing substance is selected in such a way that its excitation range lies in an excitation range of a tissue-autofluorescence of tissue surrounding said endoscopic instrument, said light source is selected in a way that it only emits light of specific wavelength ranges matching excitation ranges of both said fluorescent marking of said instrument and said tissue autofluorescence of the tissue surrounding said endoscopic instrument, therefore said same light source can excite both fluorescence phenomena.

24. The endoscopic system of claim 23, wherein said fluorescing substance can be excited in a range from 400 nm to 500 nm.

25. The endoscopic system of claim 23, wherein said marking is configured as a marking element applied on said endoscopic instrument.

26. The endoscopic system of claim 25, wherein said marking element is applied removably.

27. The endoscopic system of claims 23, wherein said at least one distal working element is equipped with a marking.

28. The endoscopic system of claim 27, wherein two working elements are present and are configured as two mouth parts that are each equipped with a marking.

29. The endoscopic system of claim 23, wherein a marking is respectively provided both on said at least one working element and in a distal end section of said shaft.

30. The endoscopic system of claim 23, wherein said shaft is configured as a tubular shaft, and wherein, said marking is configured as a tubular bushing that can be slid onto said tubular shaft.

31. The endoscopic system of claim 23, wherein said marking is provided with a coating, made of a transparent material, that covers said fluorescing substance.

32. The endoscopic system of claim 23, wherein said marking is configured as a marking element applied on said endoscopic instrument, said marking element can be inserted into a body on which an endoscopic procedure is being performed, and said marking element can be anchored there.

33. The endoscopic system of claim 23, wherein said fluorescing substance is selected from the group consisting of fluorescein, eosin, the porphyrins, cadmium sulfide, aminolevulinic acid, aminolevulinic acid hydrochloride, Acridine Orange, tetracyclines, auramine, rhodamine B, rhodamine G, auramine Carbol Fuchsin, and Nile Blue sulfate.

34. The endoscopic system of claim 23, wherein multiple markings with differently excitable fluorescing substances are provided.

35. The endoscopic system of claim 23, wherein multiple markings containing different concentrations of said fluorescing substance are present.

36. The endoscopic system of claim 23, wherein said marking is configured as a marking element that can be inserted into a body on which an endoscopic procedure is being performed, and can be anchored there, and wherein said marking element has a fluorescing substance corresponding to said of a further marking element inserted into said body.

37. The endoscopic system of claim 23, further containing a light-supplying apparatus and an endoscopic observation instrument that is connected to a light source, selected in such a way that said fluorescing substance can be excited to fluoresce by said light source.

38. The endoscopic system of claim 37, wherein said observation instrument is an endoscope.

39. The endoscopic system of claim 38, wherein said endoscope is equipped with an endoscopic camera.

40. The endoscopic system of claim 39, wherein there is provided downstream from said endoscopic camera an image processing system that continuously detects said fluorescing markings in an endoscopic image.

41. The endoscopic system of claim 23, wherein at least one endoscopic manipulation instrument is provided, through which an observation element can be introduced into a body, and at least one marking with a fluorescing substance corresponding to the marking of said endoscopic instrument is provided on an inner side of said manipulation instrument.

42. The endoscopic system of claim 41, wherein said manipulation instrument is a trokar and said observation element is an endoscope.

43. The endoscopic system of claim 40, wherein said light source emits pulsed light at least in a spectral excitation range of the fluorescing substance, and a pulse frequency corresponds to a video image frequency of said endoscopic camera.

44. The endoscopic system of claim 42, wherein said observation instrument has, at a distal end thereof, a transparent element having a fluorescing substance.

* * * * *